(12) United States Patent
Massari et al.

(10) Patent No.: US 9,442,089 B2
(45) Date of Patent: Sep. 13, 2016

(54) ANALYTE METER TEST STRIP DETECTION

(71) Applicant: LifeScan Scotland Limited, Inverness-shire (GB)

(72) Inventors: Rossano Massari, Monza (IT); Emanuele Pozzi, Monza (IT); Tim Lloyd, Inverness (GB); David Elder, Inverness (GB)

(73) Assignee: LifeScan Scotland Limited, Inverness (GB)

( * ) Notice: Subject to any disclaimer, the term of this patent is extended or adjusted under 35 U.S.C. 154(b) by 466 days.

(21) Appl. No.: 14/138,820

(22) Filed: Dec. 23, 2013

(65) Prior Publication Data

US 2015/0177176 A1 Jun. 25, 2015

(51) Int. Cl.
*G01N 27/327* (2006.01)
*G01N 27/30* (2006.01)
*G01N 33/487* (2006.01)

(52) U.S. Cl.
CPC ...... *G01N 27/307* (2013.01); *G01N 33/48785* (2013.01)

(58) Field of Classification Search
None
See application file for complete search history.

(56) References Cited

U.S. PATENT DOCUMENTS

| | | | |
|---|---|---|---|
| 6,509,796 B2 | 1/2003 | Nguyen et al. | |
| 6,525,330 B2 | 2/2003 | Paolini et al. | |
| 6,541,266 B2 | 4/2003 | Modzelewski et al. | |
| 7,267,948 B2 | 9/2007 | Vo-Dinh | |
| 7,491,942 B2 | 2/2009 | Black et al. | |
| 7,794,658 B2 | 9/2010 | Kermani et al. | |
| 7,943,034 B2 | 5/2011 | Diamond et al. | |
| 7,964,146 B2 | 6/2011 | Harding et al. | |
| 8,012,321 B2 | 9/2011 | Ichino et al. | |
| 8,343,092 B2 | 1/2013 | Rush et al. | |
| 8,480,580 B2 | 7/2013 | Wolpert et al. | |
| 8,532,732 B2 | 9/2013 | Shah et al. | |
| 2003/0042150 A1 | 3/2003 | Ryu et al. | |
| 2003/0203498 A1 | 10/2003 | Neel et al. | |
| 2004/0118704 A1* | 6/2004 | Wang | G01N 27/3272 205/792 |
| 2009/0120810 A1 | 5/2009 | Phan et al. | |
| 2009/0301899 A1 | 12/2009 | Hodges et al. | |
| 2010/0274112 A1 | 10/2010 | Hoss et al. | |
| 2011/0057671 A1 | 3/2011 | Welsh et al. | |
| 2011/0309846 A1 | 12/2011 | Elder et al. | |
| 2012/0067741 A1 | 3/2012 | Kranendonk et al. | |
| 2013/0084589 A1 | 4/2013 | Kraft et al. | |
| 2013/0162240 A1 | 6/2013 | Nielsen et al. | |

FOREIGN PATENT DOCUMENTS

| | | |
|---|---|---|
| WO | 2012039904 A1 | 3/2012 |
| WO | 2012091728 A1 | 7/2012 |
| WO | 2012125494 A2 | 9/2012 |
| WO | 2013098565 A1 | 7/2013 |

OTHER PUBLICATIONS

International Search Report and Written Opinion issued in related International Patent Application No. PCT/EP2014/078990, mailed Mar. 23, 2015, 11 pages.

\* cited by examiner

*Primary Examiner* — J. Christopher Ball

(57) ABSTRACT

An analyte meter having a test strip port is configured to detect an inserted test strip using an unpowered grounded op amp while the analyte meter is in sleep mode. After a test strip is inserted and the meter is activated, the op amp is powered and provides the sample current for measuring an analyte concentration in the sample.

20 Claims, 4 Drawing Sheets

ANALYTE METER TEST STRIP DETECTION

TECHNICAL FIELD

This application generally relates to the field of blood analyte measurement systems and more specifically to a portable analyte meter that is configured to efficiently detect insertion of a test strip into a strip port circuit without adding unnecessary switching devices to the circuit.

BACKGROUND

Blood glucose measurement systems typically comprise an analyte meter that is configured to receive a biosensor, usually in the form of a test strip. Because many of these systems are portable, and testing can be completed in a short amount of time, patients are able to use such devices in the normal course of their daily lives without significant interruption to their personal routines. A person with diabetes may measure their blood glucose levels several times a day as a part of a self management process to ensure glycemic control of their blood glucose within a target range. A failure to maintain target glycemic control can result in serious diabetes-related complications, including cardiovascular disease, kidney disease, nerve damage and blindness.

There currently exist a number of available portable electronic analyte measurement devices (test meters) that are designed to activate automatically upon detecting the insertion of a test strip. In at least some of these devices electrical contacts in the meter establish connections with contact pads on the test strip, which cause a voltage fluctuation in a detection circuit of the meter. This resulting voltage change signals the microcontroller in the meter to activate resident electronic circuits as part of a "wake up" sequence in preparation for performing an assay when a sample is applied to the inserted test strip. Typically, electronic switches in the meter disconnect, or deactivate, the detection circuit in order to change over from a test strip detection mode to an analyte measurement mode. The electronic switches themselves draw, or leak, current even when they are deactivated which creates an unwanted noise source during the analyte measurement. The very small level of electric current that is generated and analyzed during an assay sequence may be affected by these leakage currents. Hence, it would be advantageous to implement a more efficient detection circuit that does not require devices that inherently leak current.

BRIEF DESCRIPTION OF THE DRAWINGS

The accompanying drawings, which are incorporated herein and constitute part of this specification, illustrate presently preferred embodiments of the invention, and, together with the general description given above and the detailed description given below, serve to explain features of the invention (wherein like numerals represent like elements).

MODES OF CARRYING OUT THE INVENTION

The following detailed description should be read with reference to the drawings, in which like elements in different drawings are identically numbered. The drawings, which are not necessarily to scale, depict selected embodiments and are not intended to limit the scope of the invention. The detailed description illustrates by way of example, not by way of limitation, the principles of the invention. This description will clearly enable one skilled in the art to make and use the invention, and describes several embodiments, adaptations, variations, alternatives and uses of the invention, including what is presently believed to be the best mode of carrying out the invention.

As used herein, the terms "patient" or "user" refer to any human or animal subject and are not intended to limit the systems or methods to human use, although use of the subject invention in a human patient represents a preferred embodiment.

The term "sample" means a volume of a liquid, solution or suspension, intended to be subjected to qualitative or quantitative determination of any of its properties, such as the presence or absence of a component, the concentration of a component, e.g., an analyte, etc. The embodiments of the present invention are applicable to human and animal samples of whole blood. Typical samples in the context of the present invention as described herein include blood, plasma, serum, suspensions thereof, and haematocrit.

The term "about" as used in connection with a numerical value throughout the description and claims denotes an interval of accuracy, familiar and acceptable to a person skilled in the art. The interval governing this term is preferably ±10%. Unless specified, the terms described above are not intended to narrow the scope of the invention as described herein and according to the claims.

Figure 1:
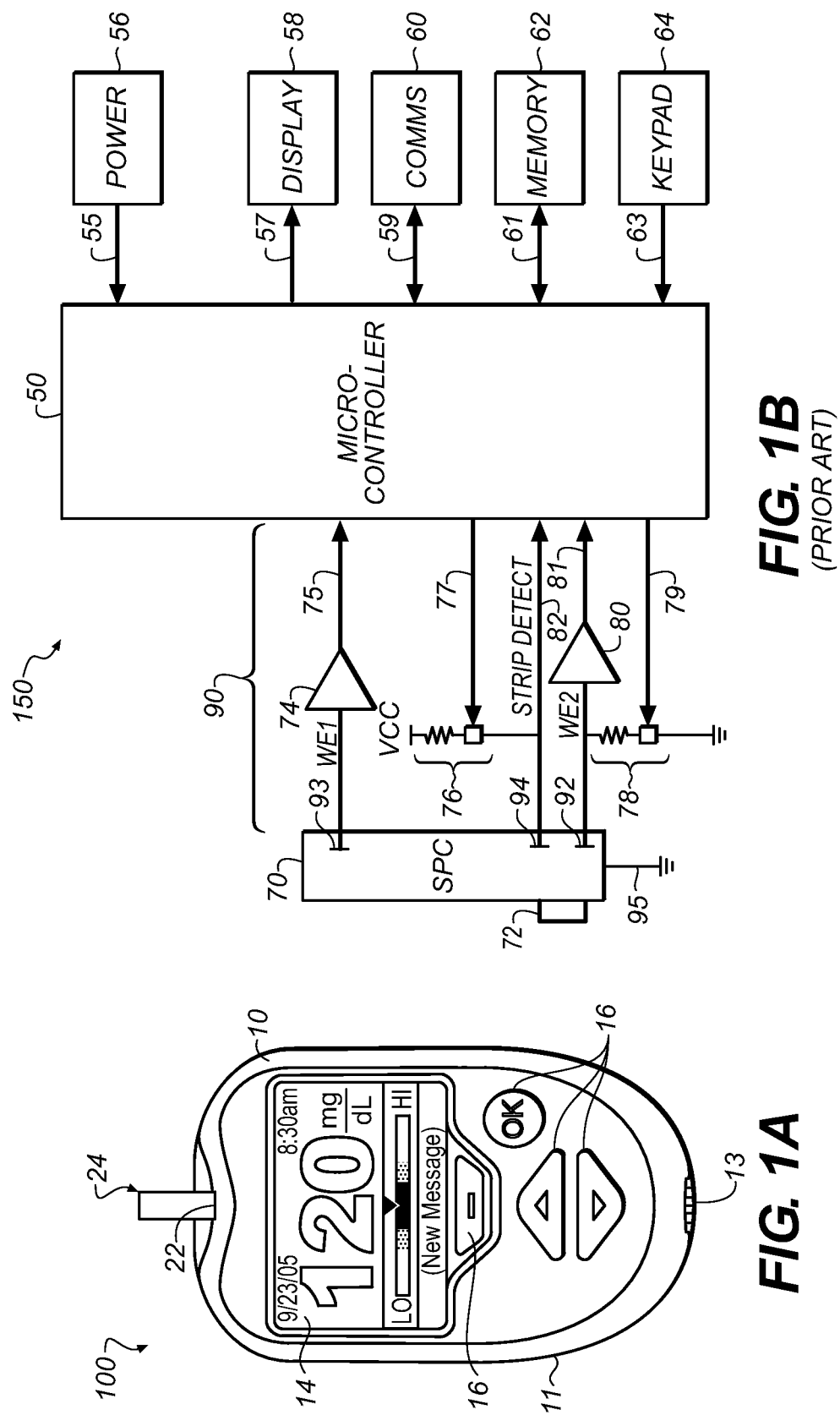
FIG. 1A illustrates a diagram of an exemplary test strip based blood analyte measurement system.
FIG. 1B illustrates a diagram of an exemplary processing system of the test strip based blood analyte measurement system of FIG. 1A.

With reference to FIGS. 1A-1B there is illustrated an analyte measurement system 100 that includes an analyte (or test) meter 10. The analyte meter 10 is defined by a housing 11 having an interior that is sufficiently sized to retain a data management unit 150 (FIG. 1B), the housing having a test strip port 22 for receiving a test strip 24. According to one embodiment, the analyte meter 10 may be a blood glucose meter and the test strip 24 is provided in the form of a glucose test strip 24 inserted into the test strip port 22 for performing blood glucose measurements. The analyte meter 10 according to this embodiment further includes a plurality of user interface buttons, or keypad, 16, 26, and a display 14, each disposed on a front facing side of the housing 14, and a data port 13 disposed on one side of the housing opposite the test strip port 22, as illustrated in FIG. 1A. A predetermined number of glucose test strips may be stored in the housing 11 and made accessible for use in blood glucose testing. The plurality of user interface buttons 16 can be configured to allow the entry of data, to prompt an output of data, to navigate menus presented on the display 14, and to execute commands. Output data can include, for example, values representative of an analyte concentration that are presented on the display 14. User inputs may be requested via programmed prompts presented on the display 14, and a user's responses thereto may initiate command execution or may include data that may be stored in a memory module of the analyte meter 10. Specifically, and according to this exemplary embodiment, the user interface buttons 16 include markings, e.g., up-down arrows, text characters "OK", etc, which allow a user to navigate through the user interface presented on the display 14. Although the buttons 16 are shown herein as separate switches, a touch screen interface on display 14 with virtual buttons may also be utilized.

The electronic components of the glucose measurement system 100 can be disposed on, for example, a printed circuit board situated within the housing 11 and forming the data management unit 150 of the herein described system. FIG. 1B illustrates, in simplified schematic form, several of the electronic sub-systems disposed within the housing 11 for purposes of this embodiment. The data management unit 150 includes a processing unit 50 in the form of a microprocessor, a microcontroller, an application specific integrated circuit ("ASIC"), a mixed signal processor ("MSP"), a field programmable gate array ("FPGA"), or a combination thereof, and is electrically connected to various electronic modules included on, or connected to, the printed circuit board, as will be described below.

The microcontroller 50 may be electrically connected to the test strip port connector ("SPC") 70 positioned in the test strip port 22 via an analog front end sub-system 90. The analog front end 90 is electrically connected to the SPC 70 and to the microcontroller 50 during blood glucose testing. To measure a selected analyte concentration, the SPC 70 is configured to detect a resistance or impedance across electrodes disposed on the analyte test strip 24, which are electrically connected to an applied blood sample disposed in a sample chamber therein. The sample chamber forms an electrochemical cell together with the sample and, using a potentiostat or transimpedance amplifier, the microcontroller 50 converts an electric current measurement into digital form for presentation on the display 14, typically in units of milligrams per deciliter (mg/dl) or millimoles per liter (mmol/l). The microcontroller 50 can be configured to receive input from and to transmit signals to the SPC 70 via the analog front end circuit 90, as will be described herein, and may also perform a portion of the potentiostat function and the current measurement function.

The test strip 24 can be in the form of an electrochemical glucose test strip. The test strip 24 can include one or more layers made from non-conductive material, such as an inert or support material that provides structural rigidity, and further one or more conductive layers comprising working and counter electrodes disposed thereon. Test strip 24 can also include a plurality of electrical contact pads, where each electrode can be in electrical communication with at least one electrical contact pad. SPC 70 can be configured to electrically engage the electrical contact pads using flexible conductive contacts, or prongs, and form electrical communication with the electrodes. Test strip 24 can include a reagent layer that is disposed over at least one electrode forming part of the electrochemical cell of the test strip 24. The reagent layer can include an enzyme and a mediator. Exemplary enzymes suitable for use in the reagent layer include glucose oxidase, glucose dehydrogenase (with pyrroloquinoline quinone co-factor, "PQQ"), and glucose dehydrogenase (with flavin adenine dinucleotide co-factor, "FAD"). An exemplary mediator suitable for use in the reagent layer includes ferricyanide, which in this case is in the oxidized form. The reagent layer can be configured to physically transform glucose into an enzymatic by-product and in the process generate an amount of reduced mediator (e.g., ferrocyanide) that is proportional to the glucose concentration. The working electrode, or electrodes, can then be used to measure a concentration of the reduced mediator in the form of a current magnitude. In turn, microcontroller 50 can convert the current magnitude into a glucose concentration. An exemplary analyte meter performing such current measurements is described in U.S. Patent Application Publication No. US 2009/0301899 A1 entitled "System and Method for Measuring an Analyte in a Sample", which is incorporated by reference herein as if fully set forth in this application.

A display module 58, which may include a display processor and display buffer, is electrically connected to the microcontroller 50 over the communication interface 57 for receiving and displaying output data, and for displaying user interface input options under control of the microcontroller 50. The display interface is accessible via the microcontroller 50 for presenting menu options to a user of the blood glucose measurement system 100. User input module 64 may receive responsive inputs from the user manipulating buttons, or keypad 16, which are processed and transmitted to the microcontroller 50 over the communication interface 63. The microcontroller 50 may have electrical access to a digital time-of-day clock connected to the printed circuit board for recording dates and times of blood glucose measurements and user inputs, which may then be accessed, uploaded, or displayed at a later time as necessary.

A communications module 60 may include transceiver circuits for wireless digital data transmission and reception, and is electrically connected to the microcontroller 50 over communication interface 59. The wireless transceiver circuits may be in the form of integrated circuit chips, chipsets, and programmable functions operable via microcontroller 50 using on-board memory, or a combination thereof. The wireless transceiver circuits may be compatible with different wireless transmission standards. For example, a wireless transceiver circuit may be compatible with the Wireless Local Area Network IEEE 802.11 standard known as WiFi. A transceiver circuit may be configured to detect a WiFi access point in proximity to the analyte meter 10 and to transmit and receive data from such a detected WiFi access point. A wireless transceiver circuit may be compatible with the Bluetooth protocol and is configured to detect and process data transmitted from a Bluetooth hub in proximity to the analyte meter 10. A wireless transceiver circuit may be compatible with the near field communication ("NFC") standard and is configured to establish radio communication with, for example, an NFC compliant reader device capable of gathering analyte test measurements in proximity to the analyte meter 10. A wireless transceiver circuit may comprise a circuit for cellular communication with cellular networks and is configured to detect and link to available cellular communication towers.

An on-board memory module 62, that includes but is not limited to volatile random access memory ("RAM"), a non-volatile memory, which may comprise read only memory ("ROM"), non-volatile RAM (NVRAM), or flash memory, and may be connected to an external portable memory device via a data port 13, is electrically connected to the microcontroller 50 over a communication interface 61. External memory devices may include flash memory devices housed in thumb drives, portable hard disk drives, data cards, or any other form of electronic storage device. The on-board memory can include various embedded applications and programs executed by the microcontroller 50 for operation of the analyte meter 10, as explained herein. On board or external memory can also be used to store a history of a user's blood glucose measurements including dates and times associated therewith. Using the wireless transmission capability of the analyte meter 10, or the data port 13, as described herein, such measurement data can be transferred via wired or wireless transmission to connected computers or other processing devices.

A power supply module 56 is electrically connected to modules in the housing 11 and the microcontroller 50 to supply electric power thereto. The power supply module 56 may comprise standard or rechargeable batteries, or an AC power supply that may be activated when the analyte meter 10 is connected to a source of AC power. The power supply module 56 is electrically connected to the microcontroller 50 over the communication interface 55 such that microcontroller 50 can monitor a power level remaining in a battery of the power supply module 56.

In addition to connecting external storage for use by the analyte meter 10, the data port 13 can be used to accept a suitable connector attached to a connecting lead, thereby allowing the analyte meter 10 to be wired to an external device such as a personal computer. Data port 13 can be any port that allows for transmission of data, power, or a combination thereof, such as a serial, USB, or a parallel port.

With reference to prior art FIG. 1B, there is illustrated the data management unit 150 having the strip port connector 70 and a portion of the front-end analog subsystem 90. The strip port connector 70 comprises at least two working electrode contacts 92, 93, and a strip-detect electrical contact 94. According to this embodiment, the electrical contacts 92-94 are each formed as prongs to connect electrically with a contact pad on the test strip 24 that is inserted into the strip port connector 70. The strip port connector 70 is configured to connect together the electrical contacts 92 and 94, when the test strip 24 is inserted, through a switch bar 72 that connects to an electrode of an inserted test strip 24. The switch bar 72 generates a signal transmitted to the microcontroller 50, indicating that a test strip 24 has been inserted in the strip port connector 70, as will now be described.

Still referring to FIG. 1B, the working electrode contact 92 is connected to an input of an operational amplifier (an op-amp) 80 and the output of the op amp is connected to the microcontroller 50 over a microcontroller interface 81. A pull-down circuit 78, e.g. a resistor and FET, is connected between the working electrode contact 92 and ground and is controlled, i.e. turned on and off, by a signal from the microcontroller 50 over an interface 79. The strip-detect electrical contact 94 is connected to the microcontroller 50 via another interface 82, which is monitored by the microcontroller 50 for detecting that a test strip has been inserted into strip port connector 70. A pull-up circuit 76, e.g. a resistor and FET, is connected between strip-detect electrical contact 94 and a voltage source Vcc, which may be set at a predetermined voltage (e.g., about 3V), and is controlled, i.e., turned on and off, by a signal from the microcontroller 50 over another interface 77.

Prior to insertion of the test strip 24 into the strip port connector 70, the microcontroller 50 is programmed to maintain the analyte measurement system 100 in a low power or passive "sleep" mode. During the low power mode, microcontroller 50 activates pull down circuit 78 and pull up circuit 76, thereby connecting the working electrode contact 92 to the ground (logical 0) and the strip detect contact 94 is maintained at a higher voltage (logical 1) by being connected to voltage source $V_{CC}$. Thus, the analog front end circuit 90 may be monitored by the microcontroller 50 as a "digital" input circuit. In practice, the resistor used in the pull-up circuit 76 is typically selected at about 100 kohm and the resistor used in the pull-down circuit 78 is typically selected at about 1 kohm.

When test strip 24 is inserted into strip port connector 70, the immediate connection between the working electrode contact 92 and the strip-detect electrical contact 94, via the switch bar 72, switches the voltage at the strip detect interface 82 from high, e.g. about 3V equivalent to a logical 1, to low, e.g. about 0V equivalent to a logical 0. This voltage drop at the microcontroller input 82 signals the microcontroller that the test strip 24 has been inserted into the strip port connector 70. In response, the microcontroller 50 initiates a programmed "wake up" routine and activates the test meter 10 for performing a sample assay. Part of the activation routine includes deactivating the pull-up and pull-down circuits 76, 78, via signals transmitted on interfaces 77, 79, respectively. The pull-up and pull-down circuits 76, 78, are not needed for performing the assay, however, their deactivation does not ensure that leakage currents through these devices are also shut off, particularly through the pull-down circuit 78 which is connected to the working electrode contact 92. At this point, the analyte meter 10 awaits application of a blood sample on the test strip 24, whereafter a current measurement through the applied sample may take place using the working electrode contacts 92, 93, (and ground voltage reference contact 95) which are each connected to the microcontroller 50 through op amp circuits 74, 80, and microcontroller interfaces 75, 81, respectively. Because the current measurements performed during this sample assay are very small—on the order of several microamps—and rely on signals traveling through the switch bar 72 and the working electrode contact 92 through op-amp output 81, any leakage currents in the deactivated pull-up circuit 76 and pull-down circuit 78 may affect the assay results obtained by introducing extraneous noise.

Figure 2:
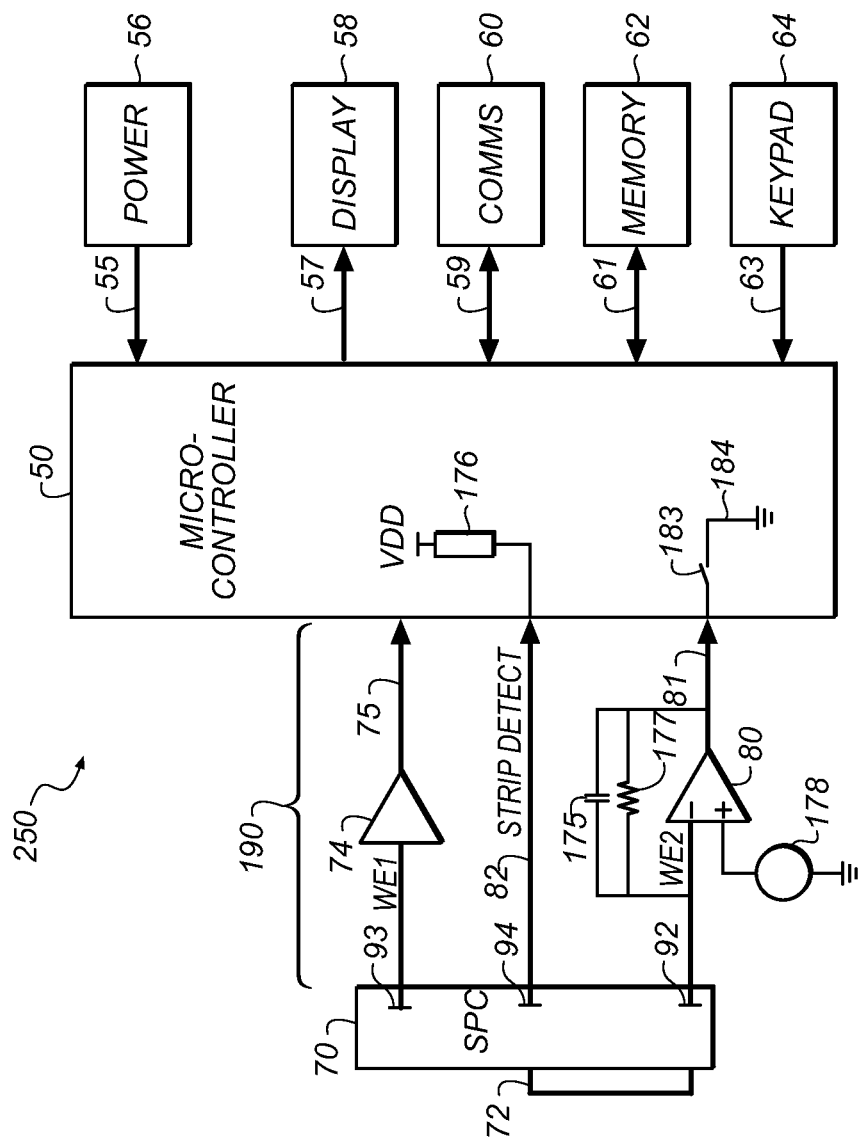
FIG. 2 illustrates a diagram of another exemplary processing system of the test strip based blood analyte measurement system of FIG. 1A.

With respect to FIG. 2, an embodiment of an exemplary data management unit (DMU) 250 having the strip port connector 70 and a portion of analog front end circuit 190 is illustrated, wherein like numbered elements operate substantially as explained above with reference to FIG. 1B, and are not repeated here for ease of description. The analog front end 190 no longer includes pull-up and pull down circuits 76, 78, attached to the strip detect interface 82 or the working electrode contact 92, thereby reducing cost of the DMU 250 and eliminating potential noise sources. The working electrode contact 92 is connected to an inverting input of the op amp 80 and the output of the op amp is connected to the microcontroller 50 over microcontroller interface 81. The microcontroller 50 includes a switch 183 connected to the microcontroller interface 81 which may be selectively coupled by the microcontroller 50 to ground 184. The strip-detect electrical contact 94 is connected to the microcontroller 50 via interface 82. The microcontroller includes a pull-up circuit 176 connected to the interface 82 which may be selectively activated by the microcontroller 50 to connect the strip-detect contact 94 to an internal power supply node comprising voltage source $V_{DD}$, which may be set at about 3V.

As noted previously and prior to insertion of the test strip 24 into the strip port connector 70, the microcontroller 50 is programmed to maintain the analyte measurement system 100 in its low power "sleep" mode. During the low power mode, the microcontroller 50 activates the pull-up circuit 176 which energizes the strip detect interface 82 and the strip detect contact 94. The microcontroller 50 further maintains the op amp 80 in an unpowered state and activates switch 183 to connect the microcontroller interface 81 to the ground 184. A voltage source 178 is connected to a non-inverting input of the op amp 80. Thereby the output of the op amp 80 is connected to the ground 184, as well as the working electrode contact 92 via the feedback circuit connected in parallel with the op amp 80. The feedback circuit comprises resistor 177 and capacitor 175 which, together with the op amp 80 and voltage source 178, form a transimpedance amplifier that is operable during an active mode of the test meter 10. Thus, the interface 82 of the analog front end circuit 190 may be monitored by the microcontroller 50 as a "digital" input signal, similar in operation to the circuit of FIG. 1B described above circuit. The size of the capacitor 175 may be selected at about 33 nF, the resistor 177 at about 220 kOhm, and the voltage source 178 may be set at about 400 mV, as an example.

When the test strip 24 is inserted into strip port connector 70 the connection between the working electrode contact 92 and the strip-detect electrical contact 94, via the switch bar 72, drops the voltage at the strip detect interface 82 from high, e.g. about 3V equivalent to a logical 1, to low, e.g. about 0V equivalent to a logical 0. This voltage drop at the microcontroller interface 82 signals the microcontroller that the test strip 24 has been inserted into the strip port connector 70. In response, the microcontroller 50 initiates a programmed "wake up" routine and activates the test meter 10 for performing a sample assay. Part of the activation routine includes deactivating the pull-up switch 176, powering the op amp 80, and opening the switch 183. At this point, the analyte meter 10 awaits application of a blood sample on the test strip 24, whereafter a current applied and measured through the sample may take place using the working electrode contacts 92, 93, which are each connected to the microcontroller 50 through op amp circuits 74, 80, and microcontroller interfaces 75, 81, respectively. The absence of the pull-up and pull-down circuits 76, 78, external to the microcontroller 50 means that leakage currents generated thereby do not affect the sample assay current measurement at least at the microcontroller interface 81.

In order to detect the inserted test strip 24, the test meter 10 may be programmed to periodically poll the strip detect interface 82 to determine whether a test strip is inserted therein, e.g., at approximately 1 sec intervals. The polling takes place during a sleep mode of the test meter 10 by activating the pull up circuit 176 and measuring the voltage at the interface 82 after a preselected delay. As described above, and during sleep mode, the op amp 80 is unpowered and its output at microcontroller interface 81 is connected to ground by the switch 183.

Figure 3:
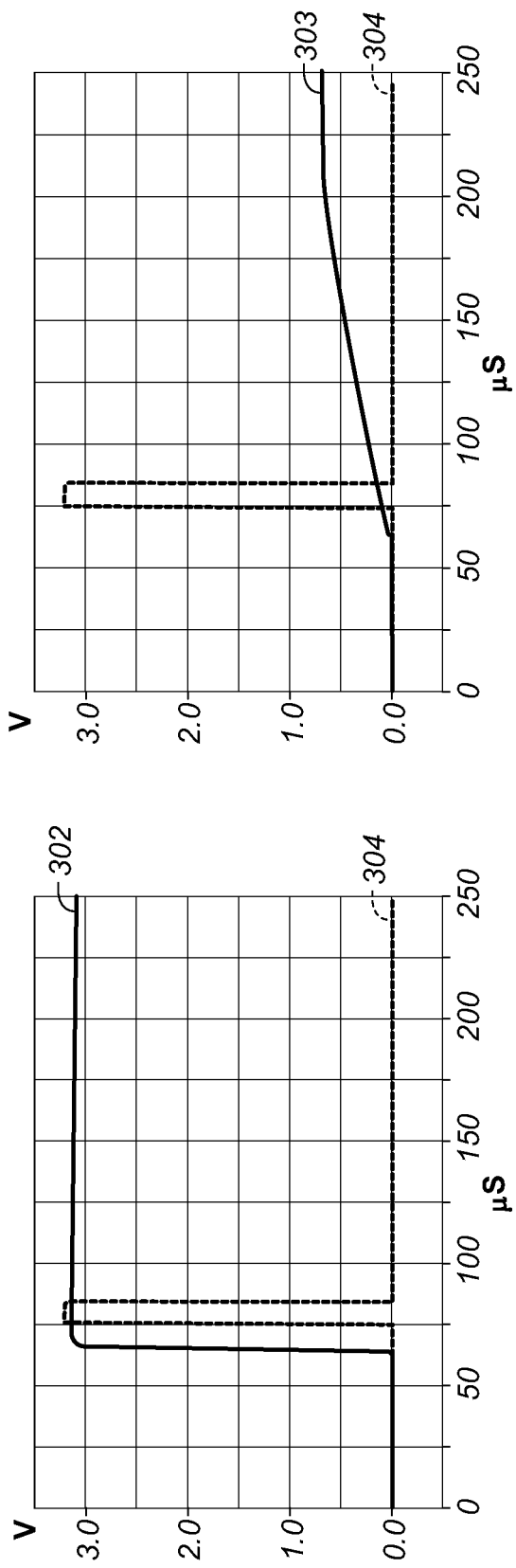
FIGS. 3A-3B illustrate an operational graph of the voltage levels monitored by the exemplary processing system of FIG. 2.

FIGS. 3A-3B illustrate the strip detect voltage levels 302, 303, on interface 82, as detected by the microcontroller 50, when a test strip 24 is not inserted (FIG. 3A) into the strip port connector 70 and when a test strip 24 is inserted (FIG. 3B) into the strip port connector 70, respectively. Referring to FIG. 3A, the polling sequence begins at about 60 is wherein the pull-up circuit 176 is activated to connect the strip detect interface 82 to voltage source $V_{DD}$, wherein the voltage level on the strip detect interface 82 rises immediately to about 3 V. After a preselected delay of about 15 is the voltage level of the strip detect interface 82 is sensed during an activation, i.e., high voltage level, of a microcontroller sense circuit measurement window 304, i.e. from about 75 is to about 85 µs. The microcontroller senses the high voltage level 302 of about 3 V (i.e. a logical or digital 1) of the strip detect interface 82 which indicates to the microcontroller 50 that a test strip has not been inserted in the strip port connector 70, which causes the microcontroller 50 to maintain the test meter in the low power sleep mode until the next poll. Referring to FIG. 3B, the polling sequence for detecting an inserted test strip begins at about 60 is wherein the pull-up circuit 176 is activated to connect the strip detect interface 82 to voltage source $V_{DD}$, as just described. After the preselected delay of about 15 µs, the voltage level of the strip detect interface 82 is sensed during an activation, i.e., high voltage level, of a microcontroller sense circuit measurement window 304, i.e. from about 75 is to about 85 µs. The microcontroller senses the low voltage level 303 of about 0.2 V (i.e. a logical or digital 0) of the strip detect interface 82 which indicates to the microcontroller 50 that a test strip has been inserted in the strip port connector 70 which causes the microcontroller 50 to initiate the wake-up activation sequence of the test meter 10 as described above. The preselected delay of about 15 is after energizing the strip-detect signal interface 82 provides a time window 304 wherein the voltage level of the strip detect interface 82 is sufficiently differentiated as between the test-strip-not-inserted voltage level 302 and the test-strip-inserted voltage level 303 so that the microcontroller 50 can digitally (logic 0/1) distinguish the difference. As shown in FIG. 3B the strip detect interface voltage 303 continues to rise after insertion of the test strip 24. Therefore, it is advantageous, for an accurate digital read, to measure the voltage level thereon earlier rather than later.

Figure 4:
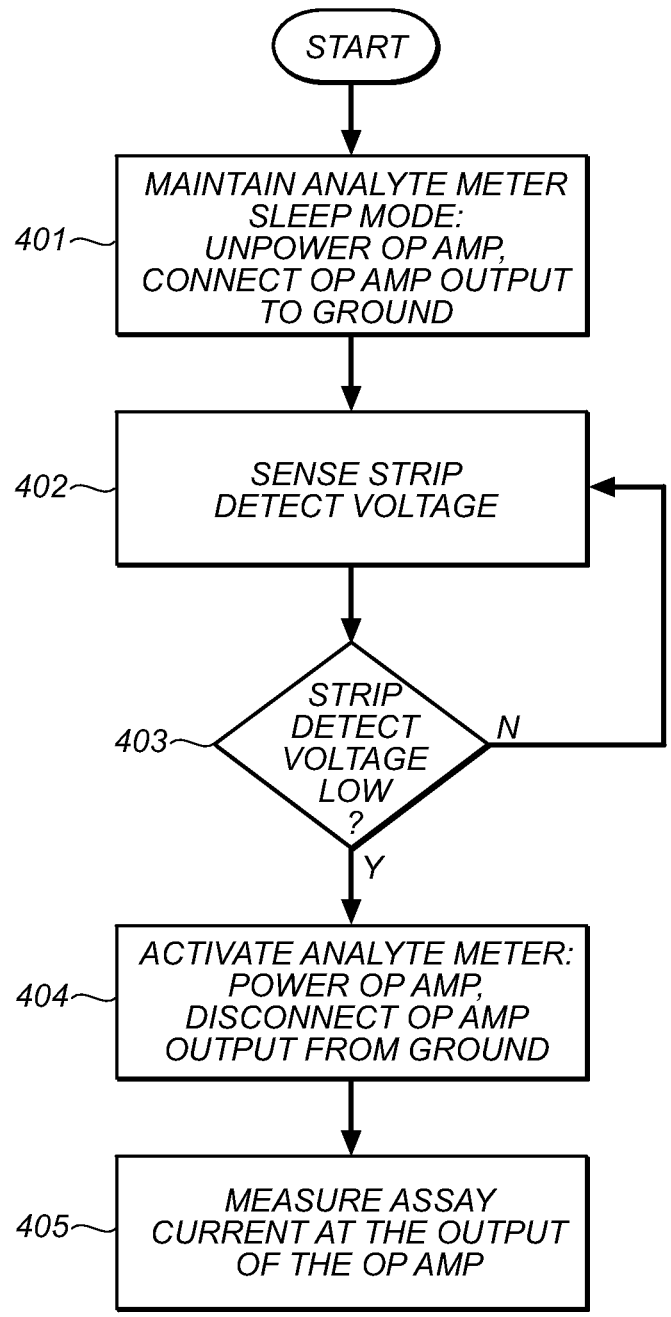
FIG. 4 illustrates a flow chart of a process performed by the exemplary processing system of FIG. 2.

With respect to FIG. 4, there is illustrated a flow chart of a method of operating an embodiment of an analyte measurement system 100. At step 401, the analyte measurement system 100 is maintained in a (default) low power inactive sleep mode. Maintenance of the sleep mode includes unpowering an op amp 80 of the test meter, such as by disconnecting or switching off its power supply and connecting an output of the op amp to ground 184. At step 402, a voltage level of a strip detect interface 82 is periodically sensed by the analyte measurement system 100. If the sensed voltage level is at a high voltage level equivalent to a digital "one", step 403, the analyte measurement system 100 is programmed to continue periodically polling the strip detect interface 82. If the sensed voltage level is at a low voltage level equivalent to a digital "zero", the analyte measurement system 100 is programmed to activate an analog front end circuit 190 to perform an analyte measurement, step 404, including powering the op amp such as by connecting it to, or switching on, its power supply and disconnecting its output from ground 184. At step 405, the analyte measurement is performed including measuring a magnitude of a current at the output 81 of the op amp 80.

As will be appreciated by one skilled in the art, aspects of the present invention may be embodied as a processing system, method, or apparatus. Accordingly, aspects of the present invention may take the form of an entirely hardware embodiment, an entirely software embodiment (including firmware, resident software, micro-code, etc.), or an embodiment combining software and hardware aspects that may all generally be referred to herein as a "circuit," "circuitry," "module," 'subsystem' and/or "system." Furthermore, aspects of the present invention may take the form of a computer program product embodied in one or more computer readable medium(s) having computer readable program code embodied thereon.

Program code and/or data representative of operations and measurements performed may be stored using any appropriate medium, including but not limited to any combination of one or more computer readable medium(s). A computer readable storage medium may be, for example, an electronic, magnetic, optical, electromagnetic, infrared, or semiconductor system, apparatus, or device, or any suitable combination of the foregoing. More specific examples of the computer readable storage medium would include the following: an electrical connection having one or more wires, a portable computer diskette, a hard disk, a RAM memory, a ROM, NVRAM, an EPROM, Flash memory, an optical fiber, a portable compact disc read-only memory (CD-ROM), an optical storage device, a magnetic storage device, or any suitable combination of the foregoing. In the context of this document, a computer readable storage medium may be any tangible, non-transitory medium that can contain, or store a program for use by or in connection with an instruction execution system, apparatus, or device.

Program code and/or data representative of operations and measurements performed may be transmitted using any appropriate medium, including but not limited to wireless, wireline, optical fiber cable, RF, etc., or any suitable combination of the foregoing.

PARTS LIST FOR FIGS. 1A-4

10 analyte meter
11 housing, meter
13 data port
14 display
16 user interface buttons/keypad
22 test strip port
24 test strip
50 microcontroller (processing unit)
55 power supply interface
56 power supply
57 display module interface
58 display module
59 communications module interface
60 communications module
61 memory module interface
62 memory module
63 buttons/keypad interface
64 buttons/keypad module
70 strip port connector
72 switch bar
74 op amp
75 microcontroller interface
76 pull-up circuit
77 microcontroller interface
78 pull-down circuit
79 microcontroller interface
80 op amp
81 microcontroller interface
82 strip detect interface
90 analog front end circuit
92 working electrode contact
93 working electrode contact
94 strip detect contact
95 ground voltage reference
100 analyte measurement system
150 data management unit
170 strip port connector
175 capacitor
176 pull-up circuit
177 resistor
178 voltage source
183 switch
184 ground
190 analog front end circuit
250 data management unit
302 strip detect voltage level, test strip not inserted
303 strip detect voltage level, test strip inserted
304 measurement window
401 step—maintain analyte meter sleep mode: unpower op amp, connect op amp output to ground
402 step—sense strip detect voltage
403 decision—Strip detect voltage low?
404 step—activate analyte meter: power op amp, disconnect op amp output from ground
405 step—measure assay current at the output of the op amp While the invention has been described in terms of particular variations and illustrative figures, those of ordinary skill in the art will recognize that the invention is not limited to the variations or figures described. In addition, where methods and steps described above indicate certain events occurring in certain order, those of ordinary skill in the art will recognize that the ordering of certain steps may be modified and that such modifications are in accordance with the variations of the invention. Additionally, certain of the steps may be performed concurrently in a parallel process when possible, as well as performed sequentially as described above. Therefore, to the extent there are variations of the invention, which are within the spirit of the disclosure or equivalent to the inventions found in the claims, it is the intent that this patent will cover those variations as well.

What is claimed is:

1. An analyte meter comprising:
    a strip port connector configured to receive an electrochemical based analytical test strip inserted therein;
    a front end circuit electrically connected to the analytical test strip, the front end circuit comprising an op amp for providing a signal at its output node corresponding to an analyte concentration of a sample applied to the analytical test strip while the op amp is powered; and
    a strip detect signal line connected to a voltage supply and to a ground, wherein the ground connection is provided through the inserted test strip and through the output node of the op amp while the op amp is in an unpowered state.

2. The analyte meter of claim 1, wherein the ground connection through the output node of the op amp comprises a feedback circuit in parallel with the op amp.

3. The analyte meter of claim 2, wherein the feedback circuit comprises a capacitor and a resistor connected in parallel.

4. The analyte meter of claim 3, wherein the analyte meter is configured with an active mode and a sleep mode, and wherein the unpowered state of the op amp corresponds to the sleep mode of the analyte meter.

5. The analyte meter of claim 3, wherein the op amp is powered by the analyte meter in response to the analyte meter sensing the ground voltage on the strip detect line.

6. The analyte meter of claim 1, wherein the voltage supply causes the strip detect signal line to be at a digital high voltage level when the test strip is not inserted in the strip port connector.

7. The analyte meter of claim 1, wherein the analyte meter is programmed to periodically sense the voltage on the strip detect signal line.

8. An analyte meter comprising:
    a strip port connector for receiving a test strip inserted therein and for measuring an analyte level of a sample in a sample chamber of the test strip;
    a working electrode circuit connectable to ground when the test strip is inserted in the strip port connector and connectable to the sample in the inserted test strip for generating a signal corresponding to the analyte level in the sample, the working electrode circuit comprising an op amp; and a microcontroller connected to an output of the op amp for receiving therefrom the signal corresponding to the analyte level in the sample and for connecting the output of the op amp to ground for generating a strip detect signal when the test strip is inserted in the strip port connector.

9. The analyte meter of claim 8, further comprising a strip detect signal line that is connected to the working electrode circuit when the test strip is inserted in the strip port connector.

10. The analyte meter of claim 9, wherein a ground voltage level comprises the strip detect signal, and wherein the strip detect signal is transmitted over the strip detect signal line to the microcontroller.

11. The analyte meter of claim 10, further comprising a sleep state wherein the op amp is unpowered and wherein the test strip is not inserted in the strip port connector.

12. The analyte meter of claim 11, wherein the strip detect signal line is at a logical 1 voltage level during the sleep state.

13. The analyte meter of claim 12, wherein the working electrode circuit further comprises a feedback circuit connected to the op amp, the feedback circuit comprising a capacitor and resistor connected in parallel.

14. The analyte meter of claim 11, wherein the microcontroller switches the analyte meter from the sleep state to an active state and powers the op amp in response to receiving the strip detect signal.

15. The analyte meter of claim 14, wherein the microcontroller disconnects the output of the op amp from the ground in response to receiving the strip detect signal.

16. The analyte meter of claim 13, wherein the working electrode circuit is connected to an inverting input of the op amp and a reference voltage source is connected to the non-inverting input of the op amp.

17. A method of operating an analyte meter having a strip port connector configured for receiving a test strip inserted therein, and a measurement circuit for measuring an analyte level of a sample in the inserted test strip, the method comprising:
   maintaining the analyte meter in a low power inactive mode in the absence of a strip detect signal being received;
   periodically monitoring a strip detect signal line for the strip detect signal, including connecting the strip detect signal line to a voltage source;
   configuring the strip detect signal line and the measurement circuit such that the inserted test strip couples the strip detect signal line to a grounded output of an op amp to generate the strip detect signal; and
   switching the analyte meter to an active mode from the low power inactive mode in response to receiving the strip detect signal.

18. The method of claim 17, wherein the step of maintaining the analyte meter in a low power inactive mode further comprises unpowering the op amp and connecting an output of the op amp to ground.

19. The method of claim 18, wherein the step of switching the analyte meter to the active mode includes powering the op amp and disconnecting its output from the ground.

20. The method of claim 19, further comprising measuring the analyte level of the sample in the inserted test strip including measuring a current level at the output of the powered op amp.

\* \* \* \* \*